United States Patent
Vicente Rojo et al.

(10) Patent No.: US 10,677,736 B2
(45) Date of Patent: Jun. 9, 2020

(54) METHOD OF DETERMINING A CHEMICAL COMPOSITION OF A SLAG PORTION

(71) Applicant: ArcelorMittal, Luxembourg (LU)

(72) Inventors: Asier Vicente Rojo, Cantabaria (ES); Artzai Picon Ruiz, Derio (ES); Sergio Rodriguez Vaamonde, Derio (ES)

(73) Assignee: ARCELORMITTAL, Luxembourg (LU)

(*) Notice: Subject to any disclaimer, the term of this patent is extended or adjusted under 35 U.S.C. 154(b) by 42 days.

(21) Appl. No.: 15/573,440

(22) PCT Filed: May 11, 2015

(86) PCT No.: PCT/IB2015/053453
§ 371 (c)(1),
(2) Date: Nov. 10, 2017

(87) PCT Pub. No.: WO2016/181185
PCT Pub. Date: Nov. 17, 2016

(65) Prior Publication Data
US 2018/0120235 A1  May 3, 2018

(51) Int. Cl.
*G01N 21/85* (2006.01)
*G01J 3/42* (2006.01)
(Continued)

(52) U.S. Cl.
CPC ............... *G01N 21/85* (2013.01); *G01J 3/14* (2013.01); *G01J 3/28* (2013.01); *G01J 3/2803* (2013.01);
(Continued)

(58) Field of Classification Search
CPC . G01N 21/85; G01N 21/31; G01J 3/40; G01J 3/42; B22D 2/001
See application file for complete search history.

(56) References Cited

U.S. PATENT DOCUMENTS

| 2004/0232339 A1 | 11/2004 | Lanoue |
| 2007/0000578 A1* | 1/2007 | Matschullat ............. B22D 2/00 148/508 |

(Continued)

FOREIGN PATENT DOCUMENTS

| DE | 102004044382 A1 | 3/2006 |
| JP | 2000146950 A | 5/2000 |

(Continued)

OTHER PUBLICATIONS

Sergio Rodriguez et al.: "Automatic Slag Characterization Based on Hyperspectral Image Processing", Emerging Technologies and Factory Automation, 2010 IEEE, Piscataway, NJ, USA, Sep. 13, 2010, pp. 1-4.

(Continued)

*Primary Examiner* — Thanh Luu
(74) *Attorney, Agent, or Firm* — Davidson, Davidson & Kappel, LLC

(57) ABSTRACT

A method of determining a chemical composition of a slag portion is provided. The method includes providing the slag portion having a surface, collecting light reflected from the surface using an optical system, obtaining a data set from the collected light, the data set at least defining a matrix containing values representative of an intensity of a part ($L_{M,\lambda}$) of the collected light, each part being collected from one of a plurality of points at one of a plurality of wavelengths, the matrix being indexed at least by: a plurality of space coordinates of the plurality of points, and a plurality of spectral parameters representative of the plurality of wavelengths. The method further includes conditioning the matrix in order to obtain a reduced set of values and performing a mathematical algorithm using the reduced set of values in order to obtain the chemical composition. A corresponding installation is also provided.

17 Claims, 2 Drawing Sheets

(51) Int. Cl.
  *G01N 21/31* (2006.01)
  *G01N 33/205* (2019.01)
  *G01N 21/3563* (2014.01)
  *G01J 3/28* (2006.01)
  *G01J 3/14* (2006.01)

(52) U.S. Cl.
  CPC .............. *G01J 3/42* (2013.01); *G01N 21/31* (2013.01); *G01N 21/3563* (2013.01); *G01N 33/205* (2019.01)

(56) References Cited

U.S. PATENT DOCUMENTS

| | | |
|---|---|---|
| 2007/0263212 A1 | 11/2007 | Mound |
| 2007/0265783 A1 | 11/2007 | Mound |
| 2009/0318815 A1* | 12/2009 | Barnes .................. A61B 5/742 600/473 |
| 2010/0053375 A1 | 3/2010 | Nagata |
| 2010/0063402 A1* | 3/2010 | Sheinis ................ A61B 5/0059 600/476 |
| 2013/0094717 A1* | 4/2013 | Janni .................... G06K 9/2018 382/110 |
| 2014/0327760 A1 | 11/2014 | Kurz et al. |

FOREIGN PATENT DOCUMENTS

| | | |
|---|---|---|
| JP | 2005201636 A | 7/2005 |
| JP | 2010055546 A | 3/2010 |
| JP | 2012098181 A | 5/2012 |
| WO | WO2004086941 A2 | 10/2004 |

OTHER PUBLICATIONS

Picon A et al.: "Fuzzy Spectral and Spatial Feature Integration for Classification of Nonferrous Materials in Hyperspectral Data", IEEE Transactions on Industrial Informatics, IEEE Service Center, New York, NY, US, vol. 5, No. 4, Nov. 1, 2009, pp. 483-494.

Jing Yuanyuan et al. "Image Segmentation Research Based on Kernel Function of Support Vector Machine Algorithm", Infrared Technology, vol. 37, No. 3, Mar. 2015 (along with computer translation thereof).

* cited by examiner

METHOD OF DETERMINING A CHEMICAL COMPOSITION OF A SLAG PORTION

The present invention relates to a method of determining a chemical composition of a slag portion. The invention also relates to an installation for determining said chemical composition, and to a steel manufacturing method.

BACKGROUND OF THE INVENTION

Steel can be produced through two different routes.

The first route comprises the production of pig iron inside a blast furnace and the transformation of this pig iron into crude steel in an oxygen converter or basic oxygen furnace (BOF). The second route consists in melting scraps in an electric arc furnace (EAF) to directly produce crude steel. After any of these routes, crude steel is then refined to obtain the required chemical composition of the steel, this refining step being performed in a ladle furnace (LF).

According to the first route, pig iron coming from blast furnace is poured into an oxygen converter, possibly comprising scraps. Oxygen is blown in the converter to allow decarburization of pig iron and its transformation in liquid steel. Mineral additives, such as lime and dolomite, are also added in the converter. The transformation of pig iron consists of fast oxidation reactions induced by the contact between gaseous oxygen and molten metal, in conditions which are very far from the thermodynamic equilibrium with the other present chemical elements, manganese, silicon or phosphorus for example. Such produced oxides, together with the added mineral additives, contribute to the formation of a liquid slag, which floats on the surface of the metal bath due to its lower density. For efficient purification of the metal, the equilibrium partition coefficients of the various elements (phosphorus, sulfur, etc.) between the slag and the metal should be as high as possible, corresponding, for example, to maximum values for the ratios: LP=% Pslag/% Psteel and LS=% Sslag/% Ssteel. The determination of the slag chemical composition allows producing quality crude steel.

According to the second route, metal scraps are loaded into a furnace and melted. The energy required to melt such solid scraps is mainly provided by electric arcs produced between one or several graphite electrodes and the metallic charge. The refining reactions are quite similar to those in the oxygen converter. Oxidation of the unwanted elements is obtained by oxidized impurities in the charge, by pure oxygen injected either through lances or through nozzles in the furnace, or by atmospheric oxygen which enters via furnace orifices. The oxidized impurities form the slag.

Crude steel produced by one of the previous routes is then poured into a ladle to adjust the chemical composition of the steel. The analytical quality of the liquid metal is adjusted, including compositional trimming, not only of metallic alloying elements, but also the control of metalloids (C, H, N, O, P, S), to different degrees depending on the grade. The type and content of oxide inclusions is controlled, by deoxidation (or "killing") of the steel, generally with aluminum for sheet steels, by calcium treatment to modify their composition, and by controlled floatation. Different additives, such as lime, dolomite, fluorspar and/or various fluxes are added in the ladle furnace to perform such treatments.

As previously explained, the produced impurities form a slag floating on the surface of the molten metal. Depending on the composition of the slag, additives are added to remove remaining impurities. So the knowledge of slag composition is of primary importance in order to control the quality of the refined steel.

In the EAF process, the knowledge of the chemical composition of the slag allows knowing its basicity and oxidation. However, the chemical composition of slag is not known during the process. Samples are analyzed using spectrometers after the process is completed.

During the LF process, the degree of deoxidation and desulfuration of steel is also estimated based on the visual evaluation of slag samples and on the chemical composition of the steel. The visual appearance of the cooled down slag is still used during the process. Thus, adding ferro-alloys and other additives to the batch still has a human component due to the expertise and the subjectivity of the workers. To that end, spectroscopes are used after the process is completed. This requires additional time for the samples to be prepared.

In both cases this has an impact on the process control, with detrimental consequences on the amount of waste, productivity and production costs.

An aim of the invention is to provide a method of determining a chemical composition of a slag portion that solves or reduces at least some of the above mentioned issues, in particular that improves the productivity of the manufacturing process and remains easy to implement.

BRIEF SUMMARY OF THE INVENTION

The present invention provides a method of determining a chemical composition of a slag, the method comprising the steps of:
the slag portion, the slag portion having a surface,
collecting light reflected from the surface using an optical system,
obtaining a data set from the collected light, the data set at least defining a matrix containing values representative of an intensity of a part of the collected light, each part being respectively collected from one of a plurality of points at one of a plurality of wavelengths, the matrix being indexed at least by:
plurality of space coordinates of the plurality of points, and
a plurality of spectral parameters representative of the plurality of wavelengths,
conditioning the matrix in order to obtain a reduced set of values, and
performing a mathematical algorithm using the reduced set of values in order to obtain the chemical composition.

In other embodiments, the method comprises one or several of the following features, taken in isolation or any technical feasible combination:
plurality of spectral parameters comprises spectral parameters that are representative of wavelengths ranging from 200 nm to 20000 nm;
plurality of spectral parameters comprises spectral parameters that are representative of wavelengths ranging from 399 nm to 965 nm;
plurality of spectral parameters is representative of wavelengths that are all comprised between 399 nm and 965 nm;
step of obtaining a data set includes the following substeps:
gray scale values representative of an intensity of the parts, and
the values contained in the matrix using said gray scale values;

the step of conditioning includes a substep of normalizing each value in the matrix in order to obtain normalized values adapted to be free of an influence of an external illumination of the slag portion during the step of collecting the reflected light;

step of conditioning includes a substep of segmenting the matrix, wherein at least some of the values of the matrix are analyzed in order to determine whether the corresponding points belong to the slag portion, and wherein only the values of the matrix corresponding to points that belong to the slag portion are kept in the matrix;

step of conditioning includes a substep of spatial smoothing of the normalized values in order to obtain a spectral signature of the slag portion;

the step of conditioning includes a substep of reducing the size of the spectral signature by selecting a subset of values in the spectral signature in order to obtain the reduced set of values, the selected subset being indexed by a subset of spectral parameters selected from the plurality of spectral parameters;

the step of conditioning includes a substep of including additional parameters into the spectral signature in order to obtain a completed set of values, the additional parameters being derived from the plurality of spectral parameters the method further includes a step of training comprising a substep of providing the subset of spectral parameters using a recursive feature elimination;

step of performing a mathematical algorithm comprises a substep of regression;

the method includes a step of training comprising a substep of obtaining parameters used in the substep of regression;

regression is based on a support vector machine model; and the support vector machine has a radial basis function kernel.

The invention also deals with a method of manufacturing steel, including:

step of defining a targeted chemical composition of the steel, a step of determining a chemical composition of a portion of a slag produced during the process of steel manufacturing as defined hereabove, a step of estimation of a chemical composition of the steel using the determined chemical composition of the slag portion, a step of calculating amounts of additives using the estimated chemical composition of the steel, and a step of adding said additives in said amounts into the steel in order to reach said targeted chemical composition of the steel.

The invention also deals with an installation for determining a chemical composition of a slag portion, the installation comprising:

optical system adapted for collecting light reflected from a surface of the slag portion, means for obtaining a data set from the collected light, the data set at least defining a matrix containing values representative of an intensity of a part of the collected light, each part being respectively collected from one of a plurality of points at one of a plurality of wavelengths, the matrix being indexed at least by:

plurality of space coordinates of the plurality of points, and a plurality of spectral parameters representative of the plurality of wavelengths, means for conditioning the matrix in order to obtain a reduced set of values, and means for performing a mathematical algorithm using the conditioned reduced set of values in order to obtain the chemical composition.

In other embodiments, the installation comprises one or several of the following features, taken in isolation or any technical feasible combination:

optical system comprises at least one CCD or CMOS sensor;

the sensor is adapted for collecting light only from a segment of the surface at a time, and wherein the installation further includes a device suitable for moving the slag portion and the optical system relative to each other in order to collect light from another segment of the surface; and the optical system comprises at least one spectrograph adapted to separate each part of the collected light based on the plurality of wavelengths.

BRIEF DESCRIPTION OF THE DRAWINGS

Other features and advantages of the invention will appear upon reading the following description, given by way of example and with reference to the accompanying drawings, in which.

DETAILED DESCRIPTION

Figure 1:
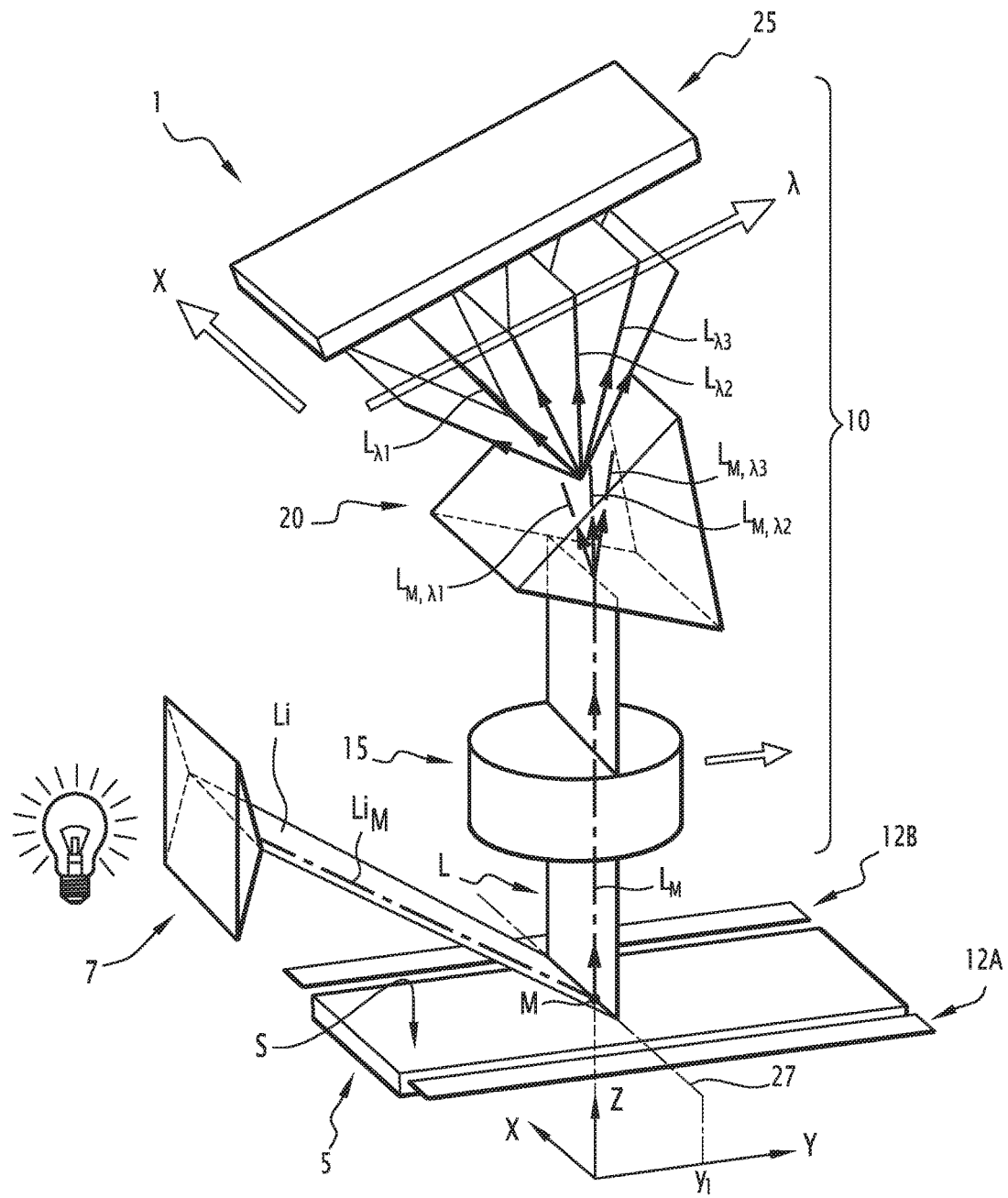
FIG. 1 is a schematic view of an installation for performing steps of a method according to the invention, in particular for collecting light.

With reference to FIG. 1, there is described an installation 1 performing steps of a method according to the invention. The installation 1 is adapted to deal on-line with a slag portion 5.

The installation 1 comprises a source of light 7, an optical system 10 adapted to collect light L from the slag portion 5, two reference standard elements 12A, 12B located next to the slag portion 5, and optionally a shifting device suitable for moving the optical system with respect to the slag portion.

The slag portion 5 is for example a sample taken from an Electrical Arc Furnace or from a Ladle Furnace.

The slag portion 5 has a chemical composition to be determined.

The physical aspect of the slag (color and thickness) is related to its chemical composition. For example, oxides such as FeO or MnO give a darker aspect to the slag, whereas oxides such as CaO or MgO increase the slag thickness.

The slag portion 5 has an upper surface S extending along two axes X, Y that are for example substantially perpendicular to each other. A third axis Z is also defined as the axis perpendicular to both the axis X and Y.

The surface S is for example horizontal.

The chemical composition is for example defined by respective mass fractions of one or several compounds taken from: $CaO$, $SiO_2$, $MgO$, $Al_2O_3$, $S$, $Fe_2O_3$, $FeO$, $F$, $MnO$, $TiO_2$, $Na_2O$, $Cr_2O_3$, $Cl$, $BaO$, $SrO$, $P_2O_5$, $K_2O$, $ZrO_2$, $ZnO$, $CuO$.

The source of light 7 is adapted for sending a light beam Li towards the slag portion 5. The light source 7 for example includes LED (light emitting diodes) and/or a halogen bulb.

The two reference standard elements 12A, 12B are for example located on either sides of the slag portion 5 along axis X, advantageously at the same level as the surface S along axis Z. The reference standard elements 12A, 12B comprise, for example, stainless steel at a mass fraction of at least 95%, for example AISI 310, with "AISI" meaning "American Iron and Steel Institute".

As a variant, a different number of reference standard element(s) is used. For example there is a single one, such as the reference standard element 12A.

The shifting device is adapted to move the optical system 10 with respect to the surface S for example along axis Y.

The optical system 10 is suitable for receiving parts $L_M$ of the light L from a plurality of points M, of which only one is represented in FIG. 1. The optical system 10 includes at least one CCD or CMOS sensor 25, at least one spectrograph 20, and at least one optical lens 15. The plurality of points M are mostly located on the surface S and on the reference standard elements 12A, 12B. The points M are advantageously regularly spaced from each other. The distance between two M points is, for example, comprised between 0.3 and 1 mm, for example 0.5 mm.

Each point M is for example identified by a first space coordinate x along axis X taken from a first plurality of space coordinate x1, x2, . . . , and by a second space coordinate y along axis Y taken from a second plurality of space coordinate y1, y2, . . . . In other words, the first plurality of space coordinates x1, x2, . . . and the second plurality of space coordinates y1, y2, . . . are representative of the plurality of points M.

The light L is for example light that is reflected by the surface S along axis Z. Surface S is lit by the light source 7. In other embodiments (not represented), the light L is conducted by means of one or multiple optic fiber cables.

The segment 27 is advantageously substantially parallel to the X axis. The segment 27 includes the points M with a same given second space coordinate y, for example y1 as shown in FIG. 1. Due to the optional movement of the optical system 10 along axis Y, the sensor 25 is suitable for scanning successive segments parallel to the segment 27 in order to advantageously cover the whole surface S.

The spectrograph 20 is for example a Specim V10_04204 imaging spectrograph. The spectrograph 20 is able to separate the parts $L_M$ of light coming from the point M based on wavelengths represented by a plurality of spectral parameters $\lambda 1$, $\lambda 2$, . . . in order to obtain parts $L_{M,\lambda 1}$, $L_{M,\lambda 2}$, . . . which impacts the sensor 25. Advantageously the spectrograph 20 is able to separate the light L coming from the whole segment 27 in order to directly obtain parts $L_{\lambda 1}$, $L_{\lambda 2}$, . . . which impact the sensor 25.

Each part $L_{M,\lambda}$ is a part of the light $L_M$ collected from one of the points M at a given wavelength represented by the spectral parameter $\lambda$.

Each part $L_\lambda$ is a part of the light L collected from the whole segment 27 at a given wavelength represented by the spectral parameter $\lambda$. Each part $L_\lambda$ contains the parts $L_{M,\lambda}$ coming from the points M that belong to the segment 27.

The spectral parameter $\lambda$ is the wavelength itself in the described example.

The plurality of spectral parameters $\lambda 1$, $\lambda 2$, . . . is representative of a plurality of wavelengths that are used to determine the chemical composition.

Advantageously the plurality of spectral parameters $\lambda 1$, $\lambda 2$, . . . is representative of wavelengths that range between 399 nm and 965 nm. For example, the plurality of spectral parameters $\lambda 1$, $\lambda 2$ . . . is representative of wavelengths that are all comprised between 399 nm and 965 nm.

Advantageously, the plurality of spectral parameters $\lambda 1$, $\lambda 2$, . . . is regularly spaced and comprises 1024 spectral parameters for example.

In other embodiments, other capturing devices than a JAI-TM-1327GE CCD camera and a Specim V10_04204 imaging spectrograph are used.

In other embodiments other hyperspectral cameras, such as HySpex or HeadWallPhotonics spectrographs, are used instead of the above mentioned ones.

The sensor 25 is adapted for capturing light L.

The sensor 25 is a CCD or CMOS sensor. The sensor 25 is a 2D (two-dimensional) one, for example an IMX174LLJ CMOS sensor.

The sensor 25 is adapted to receive the parts $L_{M,\lambda}$ of the light L and to provide values representative of an intensity of the parts $L_{M,\lambda}$.

In the example the sensor 25 is adapted to generate a block of data B(y1) (FIG. 2) using the parts $L_\lambda$ obtained from the light coming from the segment 27 corresponding to the points M having a second space coordinate equal to y1. The sensor 25 is able to generate blocks B(y2), . . . corresponding to segments defined by the points M respectively having a second space coordinate equal to y2, . . . . Altogether the blocks of data B(y) provide the values $I_{x,y,\lambda}$.

The values $I_{x,y,\lambda}$ form a three-dimensional (3D) matrix $\Lambda_{x,y,\lambda}$ (FIG. 2), wherein x is one of the first plurality of space coordinates x1, x2, . . . , y is one of the second plurality of space coordinates y1, y2, . . . , and $\lambda$ is one of the plurality of spectral parameters $\lambda 1$, $\lambda 2$, . . . . Each value $I_{x,y,\lambda}$ of the matrix $\Lambda_{x,y,\lambda}$ is for example a gray scale value.

As a variant, only the light coming from the segment 27 is used by the sensor 25. In the matrix $\Lambda_{x,y,\lambda}$ they space coordinates is for example simply removed. In this variant, the matrix is a two-dimensional matrix $\Lambda_{x,\lambda}$.

The matrix $\Lambda_{x,y,\lambda}$ is usually referred to as a "hyperspectral image," embedding several images $\Lambda_{x,y}$ taken at various wavelengths represented by the spectral parameters $\lambda 1$, $\lambda 2$, . . . .

The installation 1 also comprises at least one computer suitable for using the matrix $\Lambda_{x,y,\lambda}$ in order to determine the chemical composition of the slag portion 5.

Figure 2:
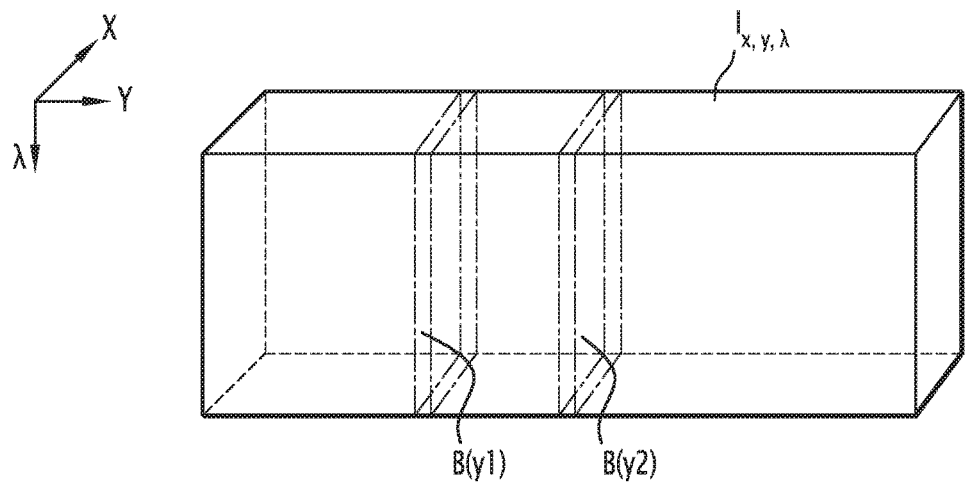
FIG. 2 is a schematic view of the three dimensional matrix defined by the method using the light collected by the installation shown in FIG. 1.
Figure 3:
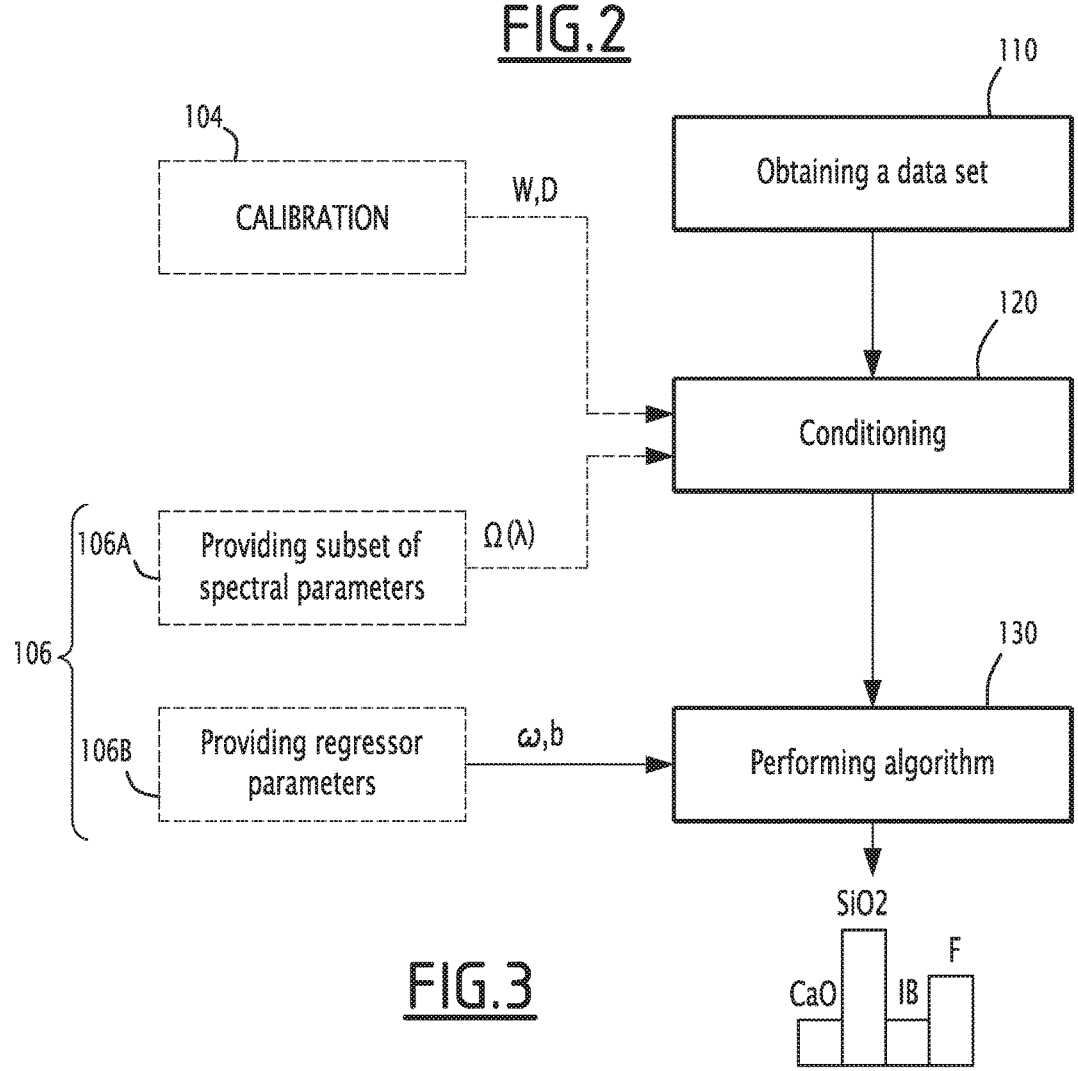
FIG. 3 is a diagram showing the main steps of the method.

With reference to FIGS. 1 to 3, a method 100 according to the invention will now be described. The method 100 aims at determining the chemical composition of the slag portion 5.

The method 100 is for example intended to be part of a steel production process in which the chemical composition of the slag portion 5 is determined in order to calculate amounts of additives to be added in steel during the process.

Indeed, based on the chemical composition of the slag portion 5 it is possible to estimate the chemical composition of the steel, and if this composition is different from the targeted final composition, necessary steps such as additives injection into steel can be taken.

The method 100 comprises a step 110 of providing a data set in the form of a three-dimensional matrix $\Lambda_{x,y,\lambda}$ that is to say the hyperspectral image, a step 120 of conditioning the matrix in order to obtain a conditioned matrix, and a step 130 of performing a mathematical algorithm using the conditioned matrix in order to obtain the chemical composition.

Advantageously the method 100 further comprises a step 104 of calibration in order to provide values useful for the conditioning step 120, and a training step 106 in order to determine parameters that are used in the conditioning step 120 and the algorithm performance step 130, The step 110 of providing the matrix $\Lambda_{x,y,\lambda}$ includes a substep of providing the slag portion 5, a substep of collecting the light L reflected from the surface S using the optical system 10, and a substep of obtaining a data set from the collected light L, the data set at least defining the matrix $\Lambda_{x,y,\lambda}$.

In the example, the data set that is obtained is the matrix $\Lambda_{x,y,\lambda}$ itself. As explained above, the optical system 10 is moved along axis Y with respect to the surface S in order to scan successive segments of the surface. For each segment, the optical system 10 provides a block of data B(y). The blocks of data B(y) altogether form the matrix $\Lambda_{x,y,\lambda}$.

In particular embodiments where the light from only one segment is used by the optical system 10, the optical system is not moved with respect to the surface S.

The step 120 of conditioning includes a substep of segmenting the matrix $\Lambda_{x,y,\lambda}$, a substep of normalizing each value $I_{x,y,\lambda}$, in the matrix, a substep of spatial smoothing of the values in order to obtain a spectral signature $Isig_\lambda$, and a substep of size reduction of the spectral signature $Isig_\lambda$.

In the substep of segmenting, the values $I_{x,y,\lambda}$, of the matrix $\Lambda_{x,y,\lambda}$ are analyzed in order to determine whether the corresponding points M belong to the slag portion 5. Only the values $I_{x,y,\lambda}$ corresponding to points M belonging to the slag portion 5 are kept in the matrix.

The values $I_{x,y,\lambda}$ are for example analyzed from x=0 to the width of the hyperspectral image, i.e. the maximum value of the first space coordinates x, in order to detect abrupt transitions from black values to white values, and vice versa. This is done for each second space coordinate y. Advantageously a derivative of the matrix $\Lambda_{x,y,\lambda}$ in a single wavelength $\lambda$ is calculated and values greater than a predetermined threshold are looked for. This allows detecting borders of the slag portion 5 in the hyperspectral image.

The substep of normalizing provides normalized values $Inorm_{x,y,\lambda}$ that are free of an influence of an external illumination of the slag portion 5 during the step of collecting the reflected light L. These values $Inorm_{x,y,\lambda}$ form a matrix $\Lambda$norm.

The normalization is for example performed by subtracting a dark reference value D (for "dark") and correcting for a white reference value W (for "white") according to the following formula or any equivalent:

$$Inorm_{x,y,\lambda} = \frac{I_{x,y,\lambda} - D}{W - D}$$

These dark D and white W reference may be obtained in a calibration step 104.

This calibration step 104 includes a substep of periodic acquisition of a set of dark reference value D and white reference value W. The dark reference value D is obtained from an image captured when the optical lens is covered. The white reference value W is obtained from a captured image of the reference standard elements 12A, 12B that are in known positions at coordinates X12A and X12B. A similar segmentation algorithms than the one described above is used for precise location of the reference standard elements 12A and 12B.

This calibration step may be performed once at the beginning of the steelmaking campaign or, in a preferred embodiment, it maybe regularly performed to update the reference values.

The normalization step using this formula allows correcting the hyperspectral image for the impact of the lighting system being not uniform in intensity along different positions x or/and among time or for modifications in the spectral response of the environmental illumination that affect the light received by the sensor 25.

The substep of spatial smoothing is adapted to provide the spectral signature $Isig_\lambda$ using the normalized values $Inorm_{x,y,\lambda}$. The spectral signature $Isig_\lambda$ is a more accurate spectral representation of the slag portion 5 as it integrates the noise and acquisition deviations within the sample.

A spatial smoothing technique is applied to the slag portion 5 within the matrix $\Lambda$norm. This technique is a computation of a spatial mean at each wavelength over the entire slag portion 5. The result is a single spectral signature $Isig_\lambda$ calculated using the following formula:

$$Isig_\lambda = \frac{1}{(N\max_x - N\min_x) + N_y} \sum_{i=N\min_x}^{N\max_x} \sum_{j=0}^{N_y} Inorm_{x,y,\lambda}(x=i, y=j)$$

wherein:

$N_y$ is the total space in the axis Y scanned by the system, and $N\max_x$, $N\min_x$ delimit the slag portion 5 along the X axis, and are calculated during the matrix $\Lambda_{x,y,\lambda}$ segmentation substep.

At the beginning of the size reduction substep, the spectral signature $Isig_\lambda$ may be advantageously completed with additional parameters, for example ratio or subtraction derived from the plurality of spectral parameters $\lambda 1$, $\lambda 2$ . . . in order to obtain a completed set of values Icomp.

In the example, the plurality of spectral parameters $\lambda 1$, $\lambda 2$, . . . represents 1024 wavelengths. However, due to Hugues effect, it is desirable to reduce the dimensionality to a subset of spectral parameters $\Omega(\lambda)$ of a few hundred wavelengths. Advantageously, the subset of spectral parameters $\Omega(\lambda)$ to be kept is determined during a sub-step of the training step 106, as described hereunder. It can also be determined through use of abacus, or any adapted method.

The training step 106 comprises a substep of providing a dataset of Icomp values acquired for a plurality of slag samples of known compositions, and two independent substeps 106A and 106B. The substep 106A aims at providing the subset of spectral parameters $\Omega(\lambda)$ to be kept in the size reduction step. The substep 106B aims at providing parameters for the algorithm performance step 130, it will be described later.

The substep 106A uses for example a recursive feature elimination technique where, in order to choose the relevant values, some elements from the completed set of values Icomp are removed. A performance parameter of the regression algorithm is for example calculated as the maximum existing correlation between the output of the method according to the invention and the chemical composition of the slag portion 5 that is obtained, for example, from a subset of the training dataset. The subset of the training dataset reaching the higher correlation defines the subset of spectral parameters $\Omega(\lambda)$ to be kept in the size reduction step.

A subset of values from the completed set of values Icomp is then selected based on the training step 106 and the non-selected values are removed from the signature. The values of the selected subset are indexed by the subset of spectral parameters $\Omega(\lambda)$ selected from the plurality of spectral parameters $\lambda 1$, $\lambda 2$, . . . , said subset of spectral parameters Ω(λ) being smaller than the plurality of spectral parameters. This allows reducing the size of Icomp in order to obtain a reduced set of values Ired.

The step 130 of performing a mathematical algorithm comprises a substep of data normalization and a substep of regression.

The substep of data normalization normalizes the reduced set of values Ired values into a predefined numerical range. This substep transforms values measured on different scales to a notionally common scale. It can be based, for example, on subtraction of a minimum value of the dataset and on division by the maximum value of the same dataset.

The regression step is performed by a regressor which mathematically maps the set of values with an estimated chemical composition values. The substep of regression is for example based on a support vector machine model (SVM). The SVM comprises two different parameters ω (support vectors) and b (offsets) that are determined in the substep 106B of the training step 140. Such parameters are known to the skilled person.

The chemical composition is for example obtained by multiplying the reduced set of values Ired by the vector ω and adding b values. This gives a number that is representative of the chemical composition.

As previously explained, the training step 106 comprises a substep of providing a dataset of Icomp values acquired for a plurality of slag samples of known compositions, and two independent sub-steps 106A and 106B. The substep 106A of providing the subset of spectral parameters Ω(λ) to be kept in the size reduction step has been previously described.

The step 106B sets the regressor parameters per each slag compounds for step 130, for example ω and b.

This substep 106B is based on an off-the-shelf method for SMV training.

Tests

This section includes validation tests that were performed. The training dataset composed of LF slag of known composition is divided, for example, into two subsets wherein the first one is used for calculating the regressor parameters and the second one is used for estimating the error and accuracy of the system. The error is obtained as the difference between the composition values obtained with a method according to the invention and the actual composition value. The composition values are expressed as a percentage.

The error values given in this report are:

$$\bar{e}_{100} = \frac{\bar{e}}{M-m} \times 100$$

$$s_{100} = \frac{s}{M-m} \times 100$$

These values show the average error and its standard deviation, both given as a percentage, where:

$\bar{e}$ is the average absolute error $s$ is the standard deviation of the absolute error M is the maximum value of the input values from the training dataset m is the minimum value of the input values from the training dataset The following table summarizes the results obtained with the slag samples using the invention versus laboratory analysis of same slag samples performed using XRF (X-ray fluorescence) by Perl technique.

TABLE 1

Error and Standard deviation results.

|  | CaO | S1O2 | Al2O3 | S | Fe2O3 | MnO |
|---|---|---|---|---|---|---|
| Maximum training value M | 75.61 | 33.07 | 8.87 | 2.80 | 9.84 | 10.02 |
| Minimum training value m | 37.09 | 10.94 | 0.43 | 0.13 | 0.45 | 0.10 |
| Average absolute error $\bar{e}$ (Composition) | 2.11 | 1.51 | 0.68 | 0.25 | 0.34 | 0.46 |
| Standard deviation s (Composition) | 2.00 | 1.68 | 0.81 | 0.22 | 0.51 | 0.71 |
| Mean error (%) | 5.47% | 6.81% | 8.05% | 9.54% | 3.61% | 4.63% |
| Standard deviation (%) | 5.19% | 7.61% | 9.55% | 8.14% | 5.39% | 7.16% |

Depending on the element, the relative standard deviation between compositions obtained with the invention and the XRF known technique range between 5% and 10%. This error assures enough precision in composition during the production process to make a quick assessment of physical state of the slag, so as to define the steel treatment strategy to reach the final process stage at lowest cost.

Thanks to the above described features, the method is fast and does not disrupt the steel production process.

The method makes it possible to predict the amounts of additives to be added to steel during production in order to obtain a predetermined steel chemical composition.

The method provides an accurate chemical composition in two to three seconds, whereas prior art methods require sending samples to a laboratory for analysis.

In order to optimize the ladle process based on the slag information, the slag analyzer system communicates and receives data from the plant, so the evolution of the ladle treatment is known at any time (steel composition, steel and slag weights, additives, temperature . . . ). These data together with the information about slag composition extracted allows conducting a global mass balance analysis at any point, so that the thermodynamic equilibrium calculations could be performed using any specific thermodynamic calculation software and the final steel and slag composition could be worked out in equilibrium conditions.

In addition, information about the various ferroalloys and fluxes additives used in the ladle furnace can be introduced in the calculation, including prices, since the system can easily set them. Therefore a complete analysis of the process in the ladle furnace could be performed.

What is claimed is:
1. A method of determining a chemical composition of a slag portion, the method comprising the steps of:
providing a slag portion, the slag portion having a surface;
collecting light reflected from the surface using an optical system;

obtaining a data set from the collected light, the data set at least defining a matrix containing values representative of an intensity of a part of the collected light, each part being respectively collected from one of a plurality of points at one of a plurality of wavelengths, the matrix being indexed at least by:
- a plurality of space coordinates of the plurality of points, and
- a plurality of spectral parameters representative of the plurality of wavelengths, conditioning the matrix in order to obtain a reduced set of values, and performing a mathematical algorithm using the reduced set of values in order to obtain the chemical composition, wherein the step of obtaining a data set includes:
providing gray scale values representative of an intensity of the parts, and obtaining the values contained in the matrix using said gray scale values, the step of conditioning includes normalizing each value in the matrix in order to obtain normalized values adapted to be free of an influence of an external illumination of the slag portion during the step of collecting the reflected light, and spatial smoothing of the normalized values in order to obtain a spectral signature of the slag portion.

2. The method according to claim 1, wherein the plurality of spectral parameters comprises spectral parameters that are representative of wavelengths ranging from 200 nm to 20000 nm.

3. The method according to claim 2, wherein the plurality of spectral parameters includes spectral parameters that are representative of wavelengths ranging from 399 nm to 965 nm.

4. The method according to claim 3, wherein the plurality of spectral parameters is representative of wavelengths that are between 399 nm and 965 nm.

5. The method according to claim 1, wherein the step of conditioning includes segmenting the matrix, wherein at least some of the values of the matrix are analyzed in order to determine whether the corresponding points belong to the slag portion, and wherein only the values of the matrix corresponding to points that belong to the slag portion are kept in the matrix.

6. The method according to claim 1, wherein the step of conditioning includes reducing the size of the spectral signature by selecting a subset of values in the spectral signature in order to obtain the reduced set of values, the selected subset being indexed by a subset of spectral parameters selected from the plurality of spectral parameters.

7. The method according to claim 6, further comprising a step of training including providing the subset of spectral parameters using a recursive feature elimination.

8. The method according to claim 1, wherein the step of conditioning includes including additional parameters into the spectral signature in order to obtain a completed set of values, the additional parameters being derived from the plurality of spectral parameters.

9. The method according to claim 1, wherein the step of performing a mathematical algorithm includes a regression step.

10. The method according to claim 9, further comprising a step of training including obtaining parameters used in the regression step.

11. The method according to claim 9, wherein the regression step is based on a support vector machine model.

12. The method according to claim 11, wherein the support vector machine model has a radial basis function kernel.

13. A method of manufacturing steel, comprising the steps of: defining a targeted chemical composition of the steel; determining a chemical composition of a portion of a slag produced during the process of steel manufacturing according to claim 1; estimating a chemical composition of the steel using the determined chemical composition of the slag portion; calculating amounts of additives using the estimated chemical composition of the steel; and adding the additives in the calculated amounts into the steel in order to reach the targeted chemical composition of the steel.

14. An installation for determining a chemical composition of a slag portion, the installation comprising:
an optical system adapted for collecting light reflected from a surface of the slag portion;
means for obtaining a data set from the collected light, the data set at least defining a matrix containing values representative of an intensity of a part of the collected light, each part being respectively collected from one of a plurality of points at one of a plurality of wavelengths, the matrix being indexed at least by:
a plurality of space coordinates of the plurality of points, and
a plurality of spectral parameters representative of the plurality of wavelengths,
means for conditioning the matrix in order to obtain a reduced set of values; and
means for performing a mathematical algorithm using the conditioned reduced set of values in order to obtain the chemical composition, wherein
the means for obtaining a data set are adapted for:
providing gray scale values representative of an intensity of the parts, and
obtaining the values contained in the matrix using said gray scale values,
the means for conditioning the matrix are adapted for:
normalizing each value in the matrix in order to obtain normalized values adapted to be free of an influence of an external illumination of the slag portion during the step of collecting the reflected light, and
spatial smoothing of the normalized values in order to obtain a spectral signature of the slag portion.

15. The installation according to claim 14, wherein the optical system comprises at least one CCD or CMOS sensor.

16. The installation according to claim 15, wherein the sensor is adapted for collecting light only from a segment of the surface at a time, and wherein the installation further includes a device suitable for moving the slag portion and the optical system relative to each other in order to collect light from another segment of the surface.

17. The installation according to claim 14, wherein the optical system comprises at least one spectrograph adapted to separate each part of the collected light based on the plurality of wavelengths.

* * * * *